(12) United States Patent
Bachur, Jr. et al.

(10) Patent No.: US 9,365,814 B2
(45) Date of Patent: Jun. 14, 2016

(54) SYSTEM AND METHOD FOR DETERMINING FILL VOLUME IN A CONTAINER

(75) Inventors: Nicholas R. Bachur, Jr., Monkton, MD (US); Timothy G. Foley, Jr., Fallston, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1207 days.

(21) Appl. No.: 12/558,064

(22) Filed: Sep. 11, 2009

(65) Prior Publication Data

US 2010/0003714 A1 Jan. 7, 2010

Related U.S. Application Data

(62) Division of application No. 11/269,100, filed on Nov. 8, 2005, now Pat. No. 7,604,985.

(60) Provisional application No. 60/626,449, filed on Nov. 10, 2004.

(51) Int. Cl.
*C12M 1/34* (2006.01)
*G01N 33/49* (2006.01)

(52) U.S. Cl.
CPC ............... *C12M 41/44* (2013.01); *C12M 41/34* (2013.01); *C12M 41/40* (2013.01); *G01N 33/4925* (2013.01)

(58) Field of Classification Search
CPC ...... C12M 41/34; C12M 41/40; C12M 41/44; G01N 33/4925; G01N 33/48735
USPC ............. 435/31–32, 34, 39, 40, 286.1, 288.7, 435/808
See application file for complete search history.

(56) References Cited

U.S. PATENT DOCUMENTS

| 4,152,213 | A | | 5/1979 | Ahnell |
| 4,733,095 | A | | 3/1988 | Kurahashi et al. |
| 4,945,060 | A | | 7/1990 | Turner et al. |
| 4,956,560 | A | * | 9/1990 | Smith et al. ................... 250/577 |
| 5,063,024 | A | | 11/1991 | Partanen et al. |
| 5,073,720 | A | | 12/1991 | Brown |
| 5,094,955 | A | | 3/1992 | Calandra et al. |

(Continued)

FOREIGN PATENT DOCUMENTS

| JP | 2002532712 A | 10/2002 |
| JP | 2002323503 A | 11/2002 |

(Continued)

OTHER PUBLICATIONS

Welby-Sellenriek et al. "Comparison of the BacT/Alert FAN Aerobic and the Difco ESP 80A Aerobic Bottles for Pediatric Blood Cultures." Journal of Clinical Microbiology, May 1997, pp. 1166-1171.*
PCT Search Report (WO 2006/053208) dated Mar. 24, 2006.
"BacT/Alert Blood Collection Adapter for in vitro diagnostic use Test Procedure" (Organon Teknika Corp. 1994).
"BacT/Alert Blood Culture Collection" (BioMerieux, Inc. 2003).
Automated Blood Culture: BACTEC™ 9240/9120/9050 (2001).

(Continued)

*Primary Examiner* — William H Beisner
(74) *Attorney, Agent, or Firm* — Lerner, David, Littenberg, Krumholz & Mentlik, LLP

(57) ABSTRACT

A system and method for detecting a pathogen in a sample is provided, the system capable of measuring the volume of a sample in a container through the use of various measurement technologies, thereby ensuring that a user is aware of volumes not meeting specification and/or allowing correction of results to account for the out-of-specification sample.

21 Claims, 14 Drawing Sheets

(56) References Cited

U.S. PATENT DOCUMENTS

| | | | |
|---|---|---|---|
| 5,164,796 | A | 11/1992 | Di Guiseppi et al. |
| 5,217,876 | A | 6/1993 | Turner et al. |
| 5,272,061 | A | 12/1993 | Hasselberg |
| 5,303,585 | A | 4/1994 | Lichte |
| 5,310,658 | A | 5/1994 | Berndt |
| 5,567,598 | A | 10/1996 | Stitt et al. |
| 5,568,262 | A | 10/1996 | LaChapelle et al. |
| 5,763,265 | A | 6/1998 | Itsuzaki et al. |
| 5,856,175 | A | 1/1999 | Thorpe et al. |
| 5,863,752 | A | 1/1999 | Court et al. |
| 5,870,200 | A | 2/1999 | Berndt |
| 6,226,081 | B1 | 5/2001 | Fantone et al. |
| 6,388,750 | B1 | 5/2002 | Liu et al. |
| 6,446,020 | B1 | 9/2002 | Berndt |
| 6,448,574 | B1 | 9/2002 | Chow |
| 6,598,474 | B2 | 7/2003 | Purpura et al. |
| 6,709,857 | B2 | 3/2004 | Bachur, Jr. |
| 6,782,122 | B1 | 8/2004 | Kline et al. |
| 7,021,122 | B1 * | 4/2006 | Rosemberg et al. ......... 73/54.01 |
| 2002/0121139 | A1 | 9/2002 | Purpura et al. |
| 2002/0197708 | A1 | 12/2002 | Bachur, Jr. et al. |
| 2003/0031089 | A1 | 2/2003 | Schwarz et al. |
| 2003/0109798 | A1 | 6/2003 | Kermani |

FOREIGN PATENT DOCUMENTS

| | | |
|---|---|---|
| JP | 2003130827 A | 5/2003 |
| WO | 0036400 | 6/2000 |
| WO | 2006053208 | 5/2006 |

OTHER PUBLICATIONS

BacT/Alert® Operator Manual with BacT/VIEW Operating System for Windows (2002).

Jorgensen eta/., "Controlled Clinical Laboratory Comparison of BACTEC Plus Aerobic/F Resin Medium with BacT/Alert Aerobic FAN Medium for Detection of Bacteremia and Fungemia," 35 Journal of Clinical Microbiology 53-58 (1997).

Mermel eta/., "Detection of Bacteremia in Adults: Consequences of Culturing of Inadequate Volume of Blood," 119:4 Annals of Internal Medicine 270-272 (American College of Physicians 1993).

Reimer et al., "Update on Detection of Bacteremia and Fungemia", Clinical Microbiology Reviews, Jul. 1997, vol. 10, No. 3, pp. 444-465.

Thorpe et at. "BacT/Alert: an Automated Colorimetric Microbial Detection System", 28 Journal of Clinical Microbiology, pp. 1608-1612 (1990).

U.S. Office Action Closing Prosecution for U.S. Appl. No. 95/002,155 dated Jan. 14, 2014.

\* cited by examiner

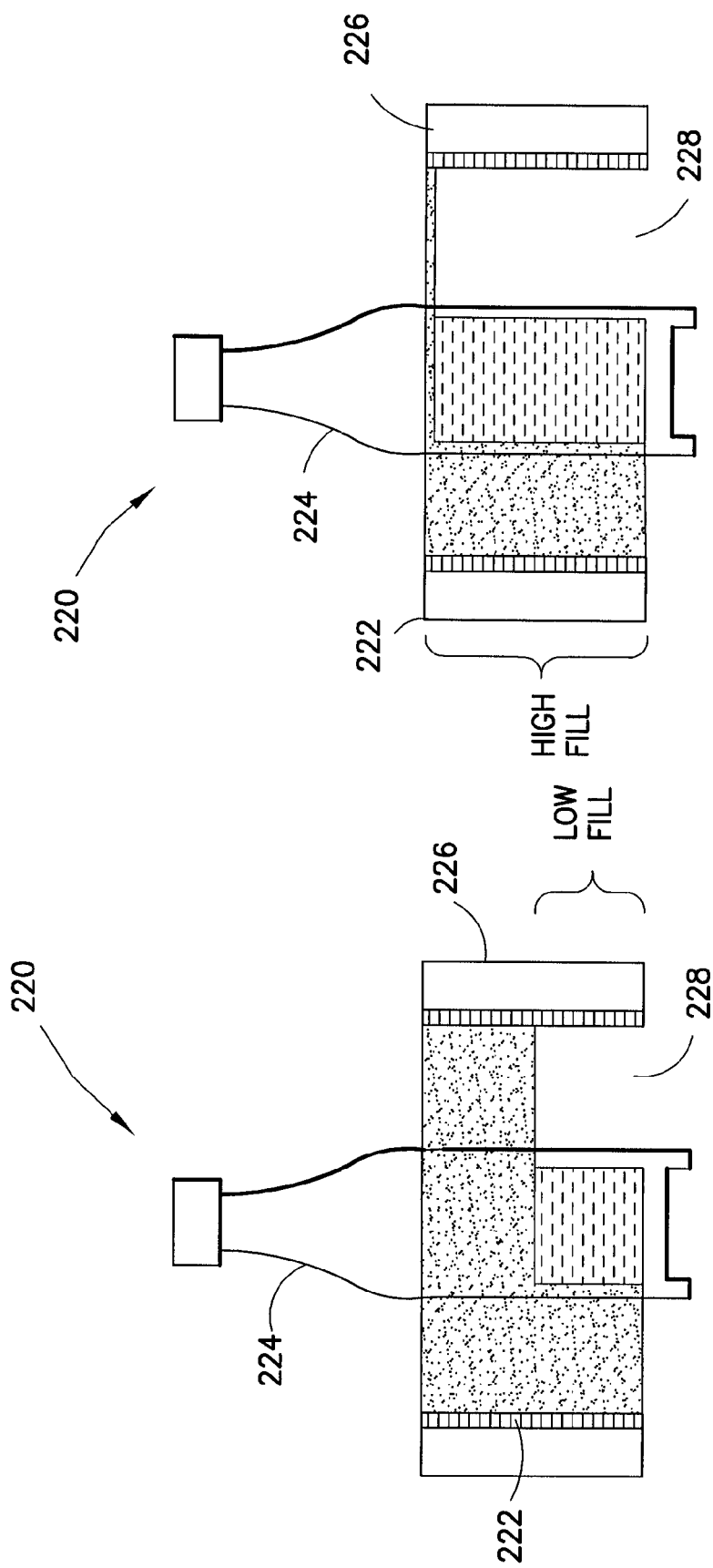

SYSTEM AND METHOD FOR DETERMINING FILL VOLUME IN A CONTAINER

This application is a divisional of U.S. patent application Ser. No. 11/269,100 filed Nov. 8, 2005, which issued as U.S. Pat. No. 7,604,985 on Oct. 20, 2009, which claims the benefit of the filing date of U.S. Provisional Patent Application No. 60/626,449, filed Nov. 10, 2004, the disclosures of which are herein incorporated by reference.

CROSS-REFERENCE TO RELATED APPLICATIONS

Related subject matter is disclosed in U.S. Pat. No. 6,709,857 of Nicholas R. Bachur, Jr. et al. entitled "System And Method For Optically Monitoring The Concentration Of A Gas In A Sample Vial Using Photothermal Spectroscopy To Detect Sample Growth", issued on Mar. 23, 2004, the entire contents of which are incorporated herein by reference.

BACKGROUND OF THE INVENTION

1. Field of the Invention

The present invention relates to a system and method for pathogen detection via culture of a biological fluid.

2. Description of the Related Art

Many medical diagnoses require that a fluid sample, such as a blood sample, be taken from a patient, cultured in a growth medium, and then examined for the presence of a pathogen believed to be causing the patient's illness. The growth medium provides nutrients that allow the pathogen, such as a bacteria, virus, mycobacteria, mammalian cells or the like, to multiply to a sufficient number so that their presence can be detected.

In some cases, the pathogen can multiply to a large enough number so that it can be detected visually. For example, a portion of the culture can be placed on a microscope slide and visually examined to detect the presence of a pathogen of interest.

Alternatively, the presence of a pathogen or other organism can be detected indirectly by detecting the presence of byproducts given off by the microorganism during its growth. For example, certain microorganisms such as mammalian cells, insect cells, bacteria, viruses, mycobacteria and fungi consume oxygen during their growth and life cycle. As the number of microorganisms increases in the sample culture, they naturally consume more oxygen. Furthermore, these oxygen consuming organisms typically release carbon dioxide as a metabolic byproduct. Accordingly, as the number of organisms present increases, the volume of carbon dioxide that they collectively release likewise increases.

Several methods exist for measuring the increase of carbon dioxide in a sample to determine whether organisms are present in the sample. For example, an instrument known as the Bactec® 9050 manufactured by Becton Dickinson and Company detects changes in the color of an indicator to determine whether carbon dioxide is present in a sample. That is, each sample is collected in a respective sample vial containing an indicator medium having a chemical that reacts to color change in the presence of carbon dioxide. A light sensor then detects the color of the indicator medium in the sample vial when the sample vial is loaded into the instrument. If the sample contains an organism which emits carbon dioxide as a function of growth and/or metabolic activity, the reflected or fluorescent intensity of the indicator medium will change in response to the presence of the carbon dioxide. The light sensor will therefore detect this change in intensity, and the instrument will indicate to an operator that an organism is present in the sample contained in the sample vial. Other examples of instruments for detecting the presence of organisms in a sample by measuring the changes in carbon dioxide in the sample are described in U.S. Pat. Nos. 4,945,060; 5,164,796; 5,094,955 and 5,217,876, the entire content of each of these patents being incorporated herein by reference.

Alternatively, instead of measuring the presence of carbon dioxide to detect the presence of an oxygen consuming microorganism, it is possible to measure depletion in the concentration of oxygen in the sample of interest. In such a system, the sample vial includes an indicator whose color or fluorescence changes as the concentration of oxygen in the vial changes. This change in color or fluorescence can be detected by an instrument, which can provide an indication to a technician that oxygen in the sample is being depleted by an oxygen consuming organism within the sample. An instrument employing such an oxygen detecting technique is described in U.S. Pat. No. 5,567,598, the entire content of which is incorporated herein by reference.

The presence of oxygen consuming organisms can also be detected by measuring a change in the pressure in a sealed sample vial containing the sample of interest. That is, as oxygen in a closed sample vial is depleted by oxygen consuming organisms, the pressure in the sealed sample vial will change. The pressure will further change in the sample vial as the organisms emit carbon dioxide. Therefore, the presence of such organisms can be detected by monitoring for changes in the pressure in the closed sample vial. Instruments that are capable of detecting such changes in pressure in the sample vial are described in U.S. Pat. Nos. 4,152,213; 5,310,658; 5,856,175 and 5,863,752, the entire content of each of these patents being incorporated herein by reference.

While existing technology is effective, improvements are always desirable.

SUMMARY OF THE INVENTION

In one embodiment, the invention relates to a method for the detection of a pathogen in a sample including the steps of, determining the volume of the sample in a sample container comprising the sample and a growth medium, then incubating the sample, and monitoring one or more parameters in the incubated sample indicative of growth of the pathogen.

In another embodiment, the invention relates to a method for the detection of a pathogen in a sample including the steps of determining the volume of a biological fluid sample in a sample container comprising the sample and a growth medium, comparing the sample volume to that of a sample volume specification, if the sample volume is outside of the sample volume specification, providing a corresponding message, responding to any user input regarding the sample, then incubating the sample, and monitoring one or more parameters in the incubated sample indicative of growth of the pathogen.

In another embodiment, the invention relates to a system for detecting a pathogen in a sample, including an incubation and measurement module adapted to receive one or more sample containers comprising a biological fluid sample and a growth medium, a sample volume sensor, separate from or part of said incubation and measurement module, the sensor adapted to measure the sample volume of said sample containers; and one or more interfaces adapted to perform one or more tasks selected from the group consisting of notifying a user if the sample containers are not within predetermined sample volume specifications, and accepting instructions on subsequent handling of the sample containers that are not within predetermined sample volume specifications.

BRIEF DESCRIPTION OF THE DRAWINGS

FIGS. 6A and 6B are conceptual schematic diagrams of a through-beam optical sensor that can be employed in the instrument shown in FIG. 2 according to an embodiment of the present invention;

Throughout the drawings, like reference numerals will be understood to refer to like parts, components and structures.

DETAILED DESCRIPTION

Figure 1:
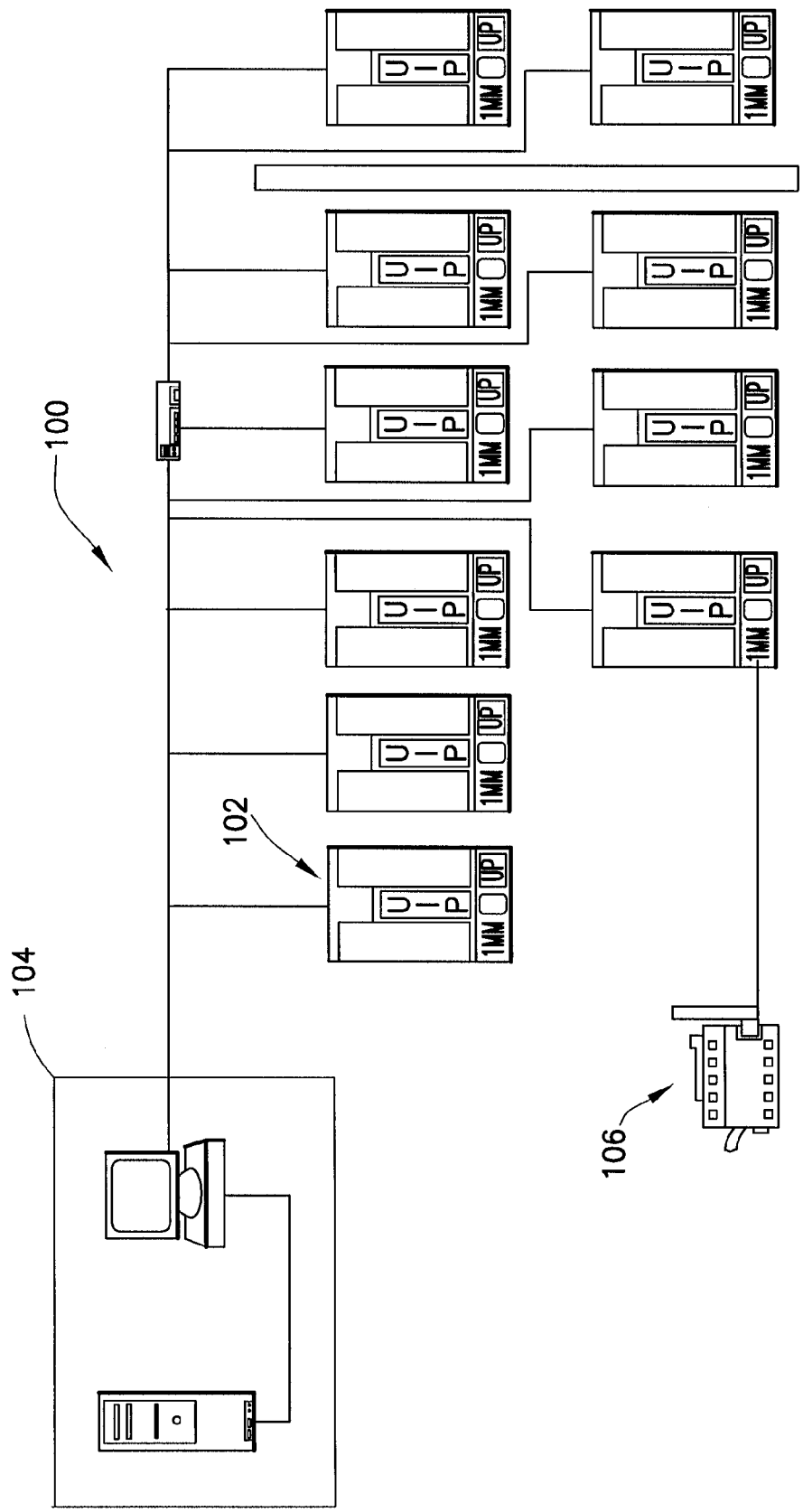
FIG. 1 is a block diagram of a system employing multiple incubation and measurement instruments according to an embodiment of the present invention.
Figure 2:
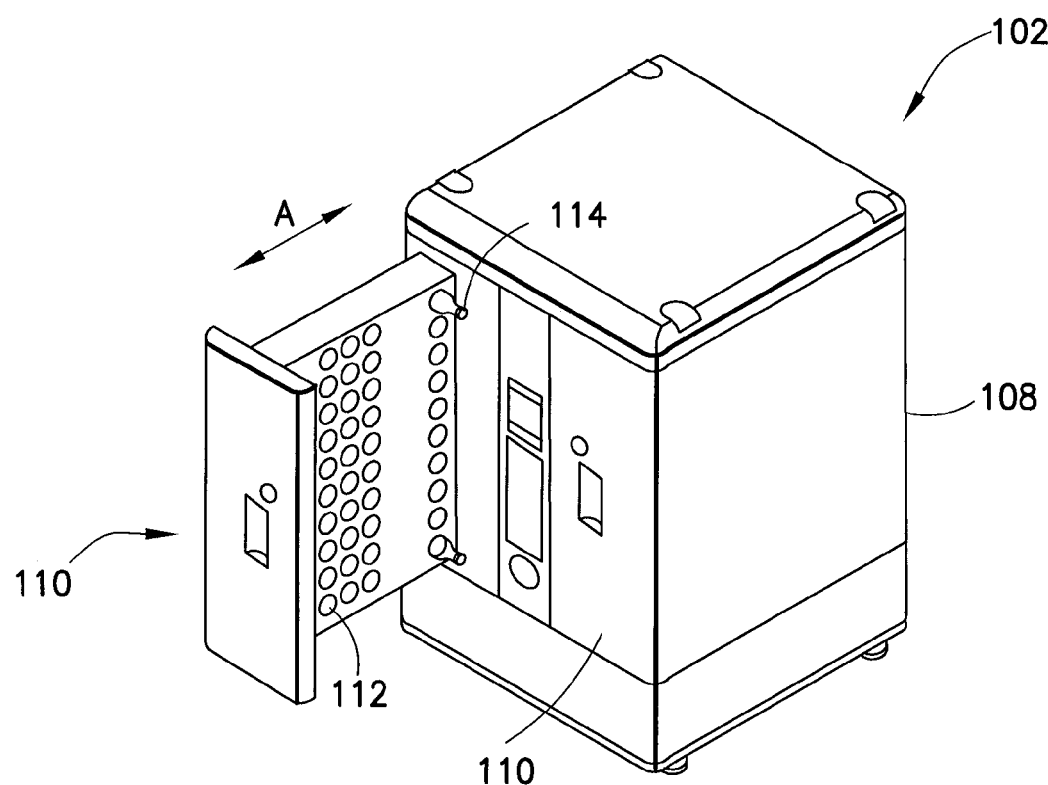
FIG. 2 is a detailed view of a measurement instrument employed in the system shown in FIG. 1 according to an embodiment of the present invention.

A system 100 for detecting growth of microorganisms in sample cultures in which a sample volume sensor according to an embodiment of the invention can be employed is shown in FIG. 1. The system 100 includes a number of measurement instruments which can each use infrared laser spectrography and/or dual wavelength modulation techniques and/or indicator media to monitor the concentration of a gas such as oxygen or carbon dioxide in sample vials, or to monitor the pressure in the sample vials, to detect microorganism growth in the vials.

As illustrated in FIG. 1, the system 100 includes a plurality of incubation and measurement modules 102 that are connected to a central computer 104. The central computer 104 can control factors, such as the incubation temperatures and times, as well as the timing of the measurements performed by the modules 102, and can further collect and classify the data readings obtained by the modules 102. The system 100 can also include a data output device, such as a printer 106, which can be controlled by the central computer 104 to print data readings obtained by the incubation and measurement modules 102.

An embodiment of the incubation and measurement module 102 is shown in FIGS. 2, 3 and 14-17. Each incubation and measurement module 102 in this embodiment includes a housing 108 and two shelves 110 that can be slid into and out of the housing 108 in a direction along arrow A. Each shelf 110 includes a plurality of openings 112, each of which is adapted to receive a sample vial 114. The openings 112 are arranged in a plurality of rows and columns as shown, and each shelf 110 can have any number of openings. For example, the openings 112 can be arranged in nine rows, with nine columns in each row, thus totaling 81 openings 112 per shelf 110.

When a sample culture is to be analyzed by the incubation and measurement module 102, the sample culture is placed in a sample vial 114. The sample vial 114 is then loaded into a respective opening 112 in the incubation and measurement module 102. In the embodiment shown, the vial 114 is a closed sample vial having any number of suitable shapes or dimensions.

The incubation and measurement module 102 can further include a keyboard, a barcode reader, or any other suitable interface that enables a technician to enter information pertaining to the sample into a database stored in a memory in the incubation and measurement module 102, in the central computer 104, or both. The information can include, for example, patient information, sample type, row and column of the opening 112 into which the sample vial 114 is being loaded, and the like.

According to the invention, the volume of a sample in the sample vial 114, is determined for example, prior to placing the sample in the incubation and measurement module 102. For example, a hospital or clinical laboratory may handle dozens of patient samples per day for a specific type of diagnostic test. These samples must be compliant with sample volume requirements so that the correct initial conditions produce validated test conditions under which the diagnostic method or system meet the manufacturer's specifications. Such compliance is required, as a number of patient samples may possibly contain relatively low concentrations of the test target that is present in the sample, and often the quantity of raw sample that is required may be quite difficult to obtain.

Patient's who are anemic, very young, very old, or quite ill may not be able to supply a sufficient quantity of a sample, such as blood, that is needed. If an insufficient raw sample is obtained, the statistical chance of recovering or detecting the target is reduced. If the amount of raw sample is excessive, the growth of the target could be suppressed and therefore hinder detection.

In a typical application, a user such as a nurse, physician, or technologist, obtains the raw sample directly from a patient. The raw sample is then transported in a test container to a laboratory where it is analyzed for the presence of pathogens, either manually by eye, or automatically by instrumentation. At this point, the invention allows one to determine whether the quantity of the raw sample is sufficient to produce reliable results. Alternatively, the sample volume may be used to determine if special measurement or analysis techniques (i.e., algorithms) should be applied in testing. Other applications of the sample volume are also possible.

Figure 4:
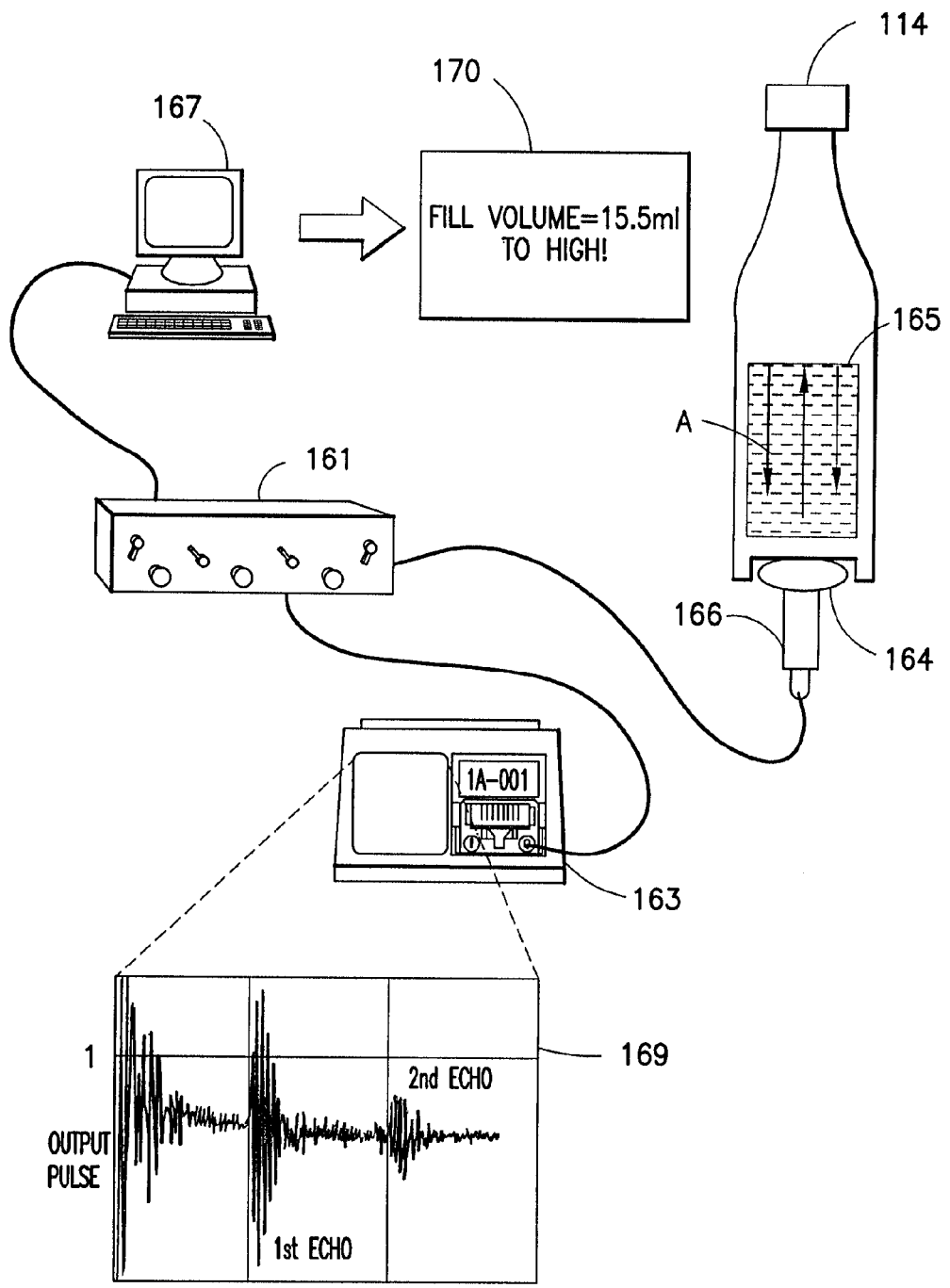
FIG. 4 is a conceptual schematic diagram of a sample volume sensor that can be employed in the instrument shown in FIG. 2 according to an embodiment of the present invention.

For example, where practical, the laboratorian can scan the sample in the test container using the apparatus of FIG. 4 to determine whether or not the sample should be tested, or whether the sample is unlikely to produce results that can be trusted. The laboratorian can thereafter provide feedback to the hospital service that supplied the sample, requesting that another sample is required and that care should be taken to assure compliance is achieved.

FIG. 4 is a schematic illustrating one embodiment of a system for determining the sample volume by detecting the height of the sample in the vial 114. Specifically, the system of FIG. 4 measures the height of the liquid inside a culture vial 114 or other sample container using an ultrasonic reflectometry apparatus (i.e., ultrasonic impulse sonar) and thereby, calculates the volume of the sample that the user introduces or inoculates.

To achieve the measurement noted above, the operator first places the previously inoculated container, vial or bottle into, for example, an appropriate receptacle in the module 102, or into a separate measuring apparatus that can be coupled to the module 102. The vial 114 remains substantially vertical and upright as it slides into a holder tube. The bottom surface of the vial 114, either glass, polymer, or other material, contacts a mildly compliant sonic coupler 164 at the bottom of the vial, which provides a waveguide for the high frequency sound from a transceiver 166, such as a 1 MHz Ultrasonic transceiver, into the vial 114.

The sound, i.e., ultrasonic impulse, travels through the outer surface of the vial 114 and then to the liquid medium 165 within the vial 114. The liquid medium 165 can include a combination of growth media and blood. This sonic wave A then travels through the liquid medium 165 within the vial 114 until part of it is reflected, as from a mirror, by the interface between the liquid and the gas above the liquid. Part of the energy of the original sonic wave A then travels back through the inner and outer wall of the vial 114 until being conducted by the compliant coupler 164 back to the transceiver 166.

A signal driver, amplifier, and processing circuit which is connected to the transceiver 166 can then measure the length of time between each event. That is, from the time that the original sonic impulse is generated, to the time that the signal reflection returns and is sensed. This length of time is proportional to the height of the liquid medium 165 inside the vial 114. Specifically, the signal driver, amplifier, and processing circuit can comprise an ultrasonic pulser/receiver 161 coupled with the transceiver 166, and which is further coupled with an oscilloscope 163 to monitor amplified transceiver output waveforms, and a computer 167 to analyze the pulse echo to determine the vial sample volume and generate a message or report. Such a report can then be provided to the user as shown by the example message 170. The oscilloscope can be used to illustrate the detected waveform signal 169 showing sound reflections as output pulse returns from the liquid to air space interface, however the oscilloscope can be replaced by signal analysis circuits and/or signal processing software. Of course, appropriate calibration and normalization can be provided during the signal processing calculations to account for differences in the liquid contained within the container, normal sample volumes, temperature fluctuations, container material, and so on, such that consistency in sample volume determination is realized.

According to the invention, therefore, the quantity of a sample that has been added to the culture vial or sample container can be determined, and this sample volume measurement data used for any number of purposes, such as to inform laboratory personnel concerning collection compliance, or to improve system performance through the foreknowledge of effects that may be expected when the sample volume is not optimal.

In the embodiment of FIG. 4, sample volume is measured using ultrasonic impulse sonar. However, in other embodiments of the invention, the measurement technique can include laser displacement sensing, through-beam optical sensing, ultrasonic reflectometry, and several other methods described in greater detail below.

Figure 5B:
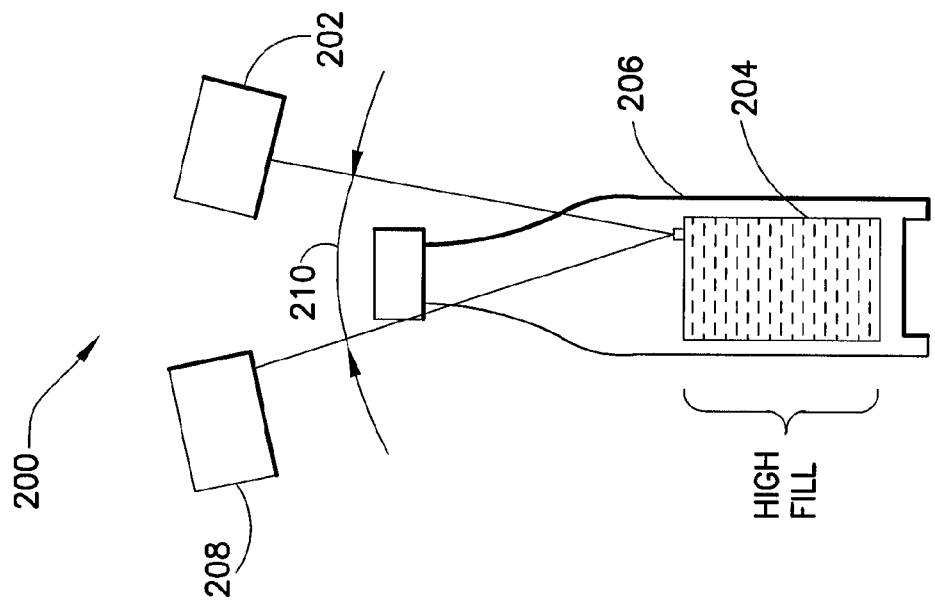
FIGS. 5A and 5B are conceptual schematic diagrams of a laser displacement sensor that can be employed in the instrument shown in FIG. 2 according to an embodiment of the present invention.
Figure 5A:
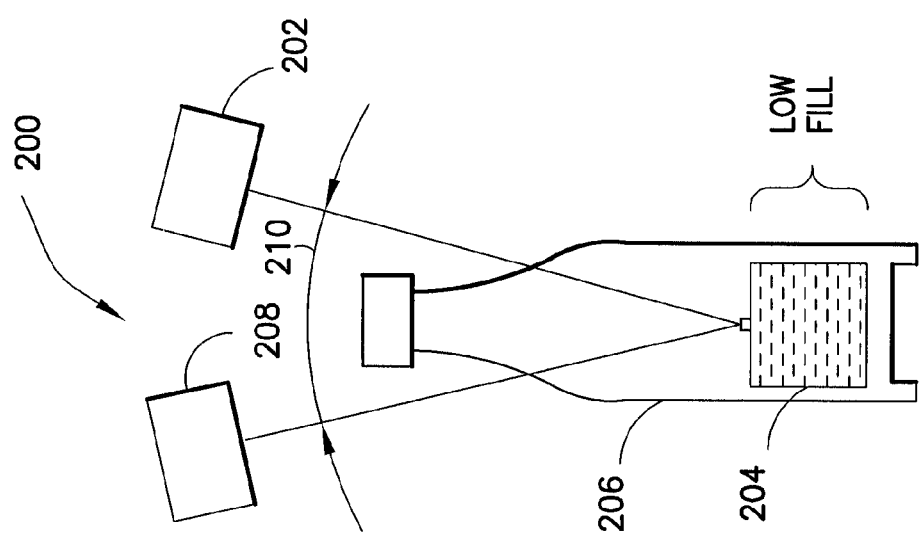

In a further embodiment, the ultrasonic impulse sonar measurement apparatus of FIG. 4 is replaced with a laser displacement sensing apparatus 200 as shown in FIGS. 5A and 5B. FIGS. 5A and 5B are conceptual schematic diagrams of a laser displacement sensor that can be employed in the instrument shown in FIG. 2. In this embodiment, a laser, such as the diode laser 202 is aimed at a given angle toward the surface of the liquid 204 within the container or blood culture vial 206. The laser beam then returns to, and is sensed by, a linear detector, such as a linear array laser displacement sensor 208, which calculates the return angle trigonometrically. As shown in FIG. 5A, the laser-spot beam angle 210 is large. In FIG. 5B, the laser-spot beam angle 210 is small. This return angle corresponds to the height of the liquid within the container (such as a low sample height as shown in FIG. 5A, a high sample height as shown in FIG. 5B, or any position therebetween) and therefore, the volume can be determined given that the size and shape of the container 206 is a known constant.

According to another embodiment, a through-beam optical sensor apparatus 220 is used to determine sample volume as shown in FIGS. 6A and 6B. FIGS. 6A and 6B are conceptual schematic diagrams of a through-beam optical sensor that can be employed in the instrument shown in FIG. 2. A light source, such as a linear light emitting diode array 222 is directed through one side of a transparent or translucent container or blood culture vial 224. A linear detector, such as a linear photodiode array or a linear imager charge coupled device (CCD) 226 on the opposite side of the container 224 detects the difference in light intensity at the meniscus, or the air/liquid boundary. A lightly shaded area 228 illustrates that the light intensity striking the linear photodiode array or CCD 226 is reduced by the contents' optical absorption. The detected interface position then indicates the fluid height (such as a low fluid height as shown in FIG. 6A, a high fluid height as shown in FIG. 6B, or any position therebetween) and hence, allows the accurate calculation of the fluid volume within the sample container.

Figure 7B:
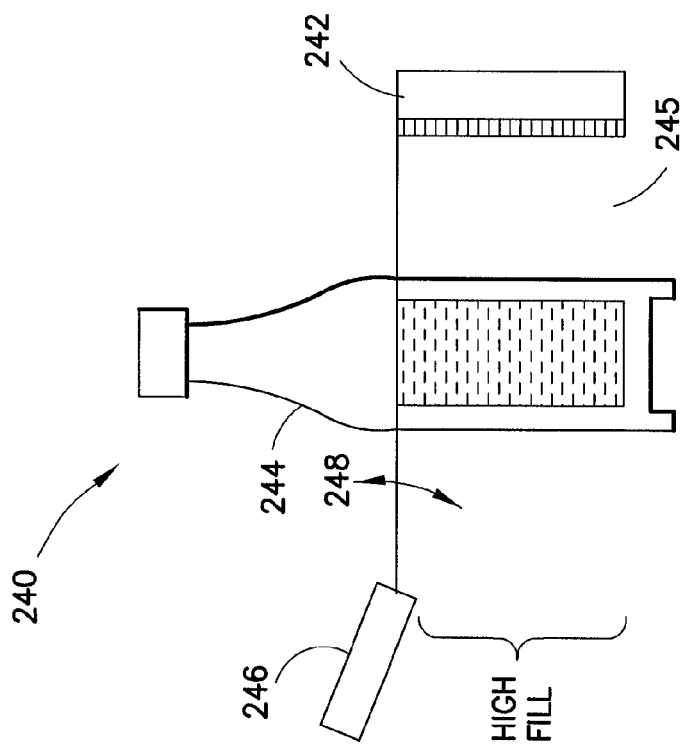
FIGS. 7A and 7B are conceptual schematic diagrams of a laser raster-scanning photodiode array that can be employed in the instrument shown in FIG. 2 according to an embodiment of the present invention.
Figure 7A:
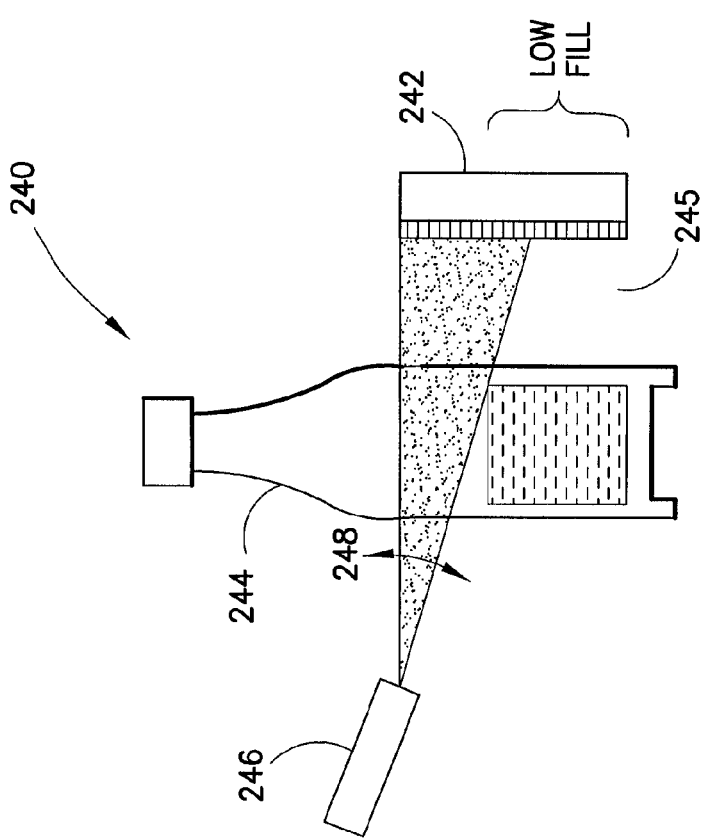

In another embodiment of the invention, a laser scanning, photodiode array 240 is used to determine sample volume as shown in FIGS. 7A and 7B. FIGS. 7A and 7B are conceptual schematic diagrams of a laser raster-scanning photodiode array that can be employed in the instrument shown in FIG. 2. A linear photodiode array or CCD 242 is placed against the transparent or translucent outer wall of a sample container or blood culture vial 244, and extends from one end to the other, across all possible sample volumes within the sample container 244. The number and density of the photosensitive elements can be increased for higher level resolution, or decreased for lower level resolution. During operation, a laser 246 is rotatably disposed adjacent to the sample container 244, and provides a scanning light through the sample container 244. The laser 246 scans the sample container 244 vertically through a rotation along a path indicated by direction arrow 248. A lightly shaded area 245 illustrates that the light intensity striking the linear photodiode array or CCD 242 is reduced by the contents' optical absorption. The resulting light intensity striking the photodiodes of array 242 is reduced by the contents' optical absorption. Accordingly, different intensity measurements detected at the array 242 can then be used to determine fluid height (such as a low fluid height as shown in FIG. 7A, a high fluid height as shown in FIG. 7B, or any position therebetween) and hence, allows the accurate calculation of the fluid volume within the sample container.

Figure 8:
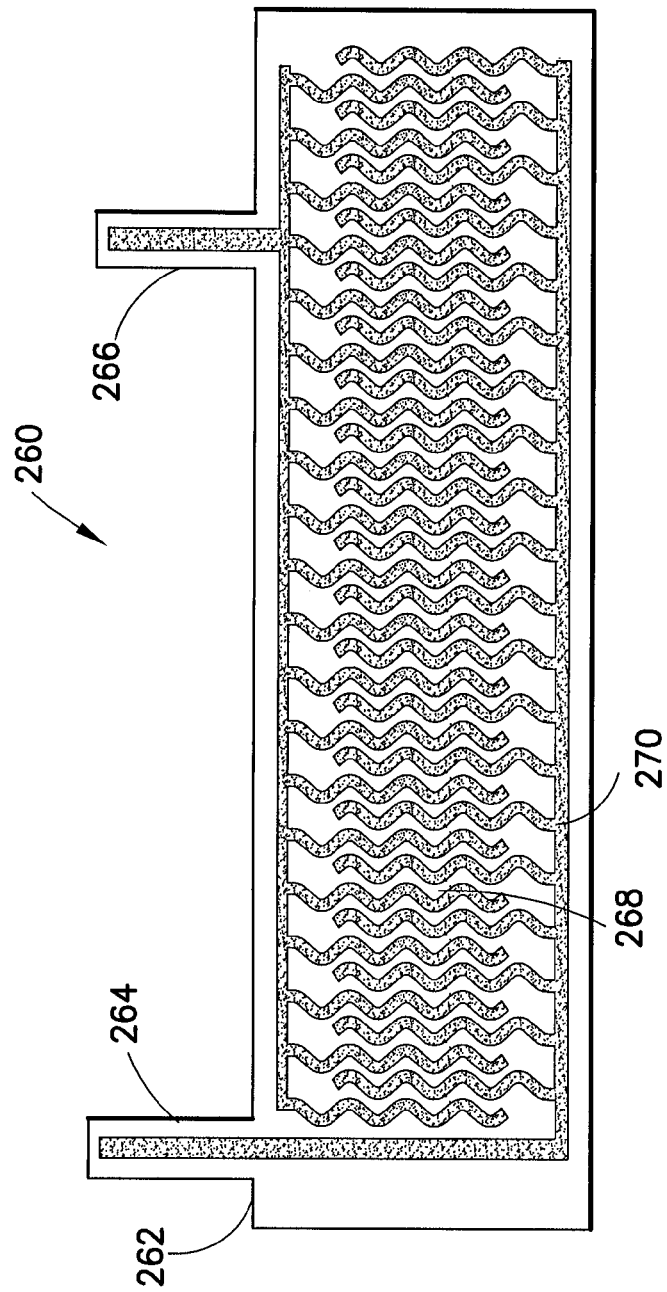
FIG. 8 is a conceptual schematic diagram of a capacitive sensor that can be employed in the instrument shown in FIG. 2 according to an embodiment of the present invention.

In still another embodiment of the present invention, a capacitive proximity detection apparatus 260 is used to determine sample volume as shown in FIG. 8. FIG. 8 is a conceptual schematic diagram of a capacitive sensor that can be employed in the instrument shown in FIG. 2. The apparatus includes electronics which rely upon the dielectric constants of air, glass, and plastic, which are used for many water-based liquid containers and which are much lower than that of the sample container contents. As the water or water-based liquid occupies an increasing volume within a capacitive sensor's dielectric space, the capacitance increases by an amount illustrated in equation (1) below.

$$C = \in S/d \tag{1}$$

In equation (1), capacitance is equal to the relative dielectric constant, $\in$, times the surface area of the capacitor's plates, S, divided by the distance between the capacitor's plates.

In this embodiment, a capacitive sensor's plates can be fabricated as a flexible circuit disposed upon a substrate 262 such as mylar or kevlar. The substrate 262 allows the flexible circuit to be placed around an exterior of a sample container and excited by an RF sine wave via a generator (not shown). The flexible circuit can be provided on the substrate 262 having a number of conductive circuit traces 270 terminating in contact tabs 264 and 266. In this example, the contact tab 264 can be configured as a ground electrode for the flexible circuit, and the contact tab 266 can be configured as a sensing electrode for the flexible circuit. The circuit traces 270 further provide gaps 268, or a dielectric space, between conductors which form the capacitive sensor. The liquid contents of the sample container around which the flexible circuit is placed then become a measurable factor within the dielectric space, that is, as long as the sample container's dimensions (such as wall thickness) are within a desired range as limited by the flexible circuit dimensions.

As the capacitance value increases due to the locally higher dielectric constant of the fluid sample container contents, a decrease in the capacitive reactance is experienced between the conductive circuit traces 270 and therefore, a measured AC current value provided to the capacitive apparatus 260 increases. This measured AC current increase can be sensed by a circuit element, such as a series drop resistor in the RF power source, and can then be used to calculate the amount of liquid level change within the sample container.

Figure 9:
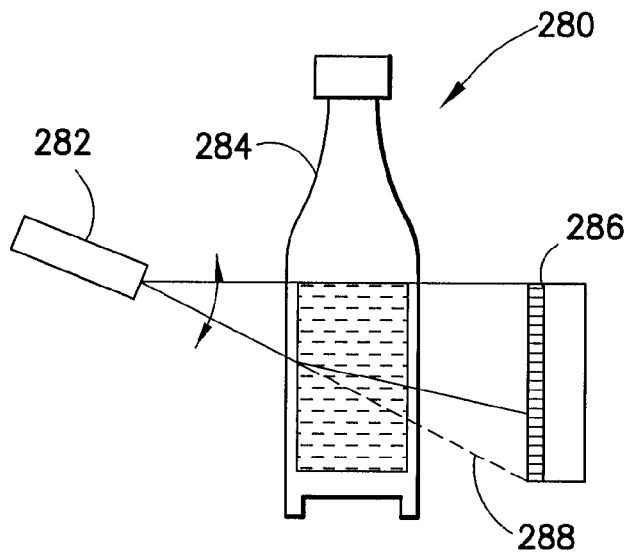
FIG. 9 is a conceptual schematic diagram of a refractive index, internal reflection detection apparatus that can be employed in the instrument shown in FIG. 2 according to an embodiment of the present invention.

In still another embodiment of the invention, a refractive index, internal reflection detection apparatus 280 is used to determine sample volume as shown in FIG. 9. A focused beam of light from either a conventional light source such as an LED, or a coherent source such as a laser 282, is directed at the side of the transparent, sample container 284 and refracts as it transmits through the air to glass, or through the air to plastic interface of the sample container wall. The walls of the sample container 284 can be made of other materials, such as crystalline quartz, silicon, borosilicate, and the like, however, as long as the wavelength of the light can be transmitted with limited diffusion or absorption by the material.

The beam of light then refracts a $2^{nd}$ time coincident with the glass or plastic to liquid interface. The angle of light refraction is dependent upon the refractive indices of the materials on either side of the interface as noted by Snell's Law illustrated in equation (2) below.

$$\sin \phi / \sin \phi' = n_1^*/n_2^* = \text{constant} \tag{2}$$

For a wave's angle of incidence, $\phi$, through a $1^{st}$ medium with a refractive index of $n_1^*$, and an angle of refraction, $\phi'$, through a $2^{nd}$ medium with a refractive index of $n_2^*$, the ratio of the two refractive indices is equal to a constant.

A photodetector array 286 can then sense the change in position of the refracted beam 288 both before and after passage through the sample container's contents to determine the position of the sample container's fluid level, or the position of the interface between the liquid and the headspace gas within the sample container 284.

In still another embodiment of the invention, a weight variation detection apparatus (not shown) is used to determine sample volume. The sample containers, which have relatively consistent weight from one to another, are measured and evaluated. Specifically, the weight of a sample container before the sample is added (known as an average weight) is determined and either stored in memory as a constant or loaded from an encoding within the barcode label. This weight can then be subtracted from the container's weight which is determined upon sample entry. This approximate change in weight is proportional to the volume of sample added to the container.

For example, in the case of blood culture vials, the average vial pre-sample weight is the sum of the container weight with cap and septum, the liquid media contents, the stirring element (if present), and the antimicrobial absorbing resin (if present). During the manufacturing process this weight can be held to within 1 gram from vial to vial. Therefore, the addition of blood to the vial during sample collection can be calculated on a per sample basis within 1 milliliter. This is adequate to assure successful recovery of bacterial cells and insure system performance.

In one implementation of the above embodiment, an operator would be directed to measure the weight of the vial during the barcode reading process. Since barcode reading is performed in the normal workflow of a laboratory-based diagnostic instrument, no additional effort is required by the operator, and the sample volume data can be acquired at the same time.

Figures 10, 11:
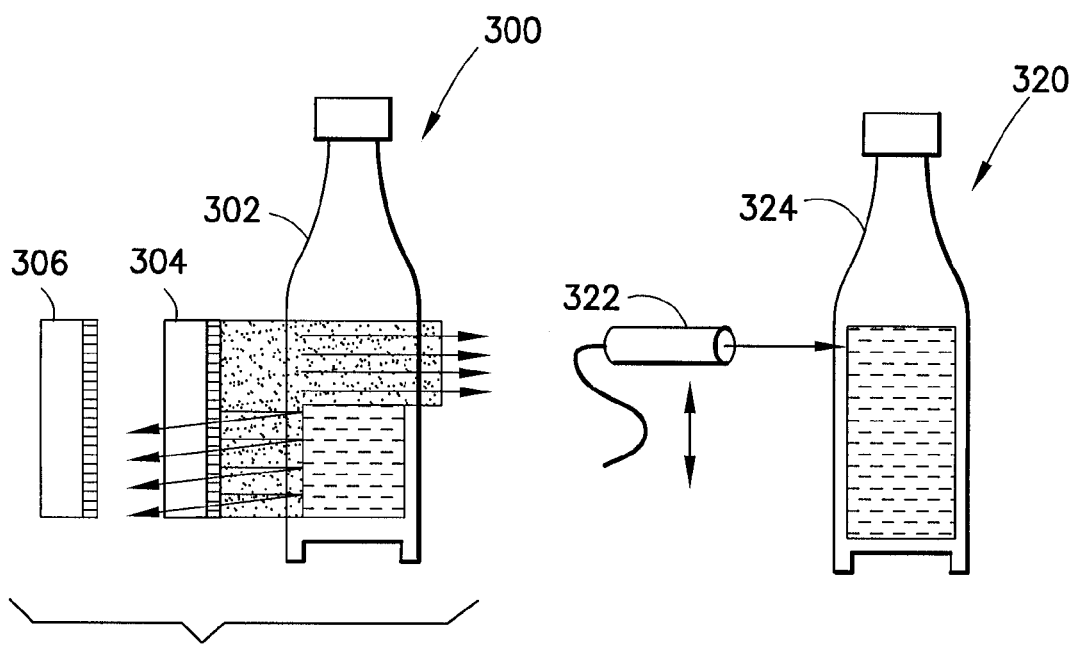
FIG. 10 is a conceptual schematic diagram of a retro-reflective optical detection apparatus that can be employed in the instrument shown in FIG. 2 according to an embodiment of the present invention.
FIG. 11 is a conceptual schematic diagram of a machine vision apparatus that can be employed in the instrument shown in FIG. 2 according to an embodiment of the present invention.

In still another embodiment of the invention, a retro-reflective optical detection apparatus 300 is used to determine sample volume shown in FIG. 10. Instead of directing the beam of light through the sample container volume as described above in regards to the through-beam optical sensor apparatus, the light beam can be sent into the side of the sample container 302, and a retro-reflective change in the light level can then be sensed at the liquid-headspace gas interface. Specifically, a light source, such as a linear light emitting diode array 304 is shown through one side of a transparent or translucent sample container or blood culture vial 302. A linear detector, such as a linear photodiode array or CCD 306 on the same side of the sample container 302, then detects the difference in levels of reflectance at the meniscus, or the air/liquid boundary. The light will have different levels of reflectance depending on the material within the sample container 302 where the beam is aimed.

In still another embodiment of the invention, a machine vision apparatus 320 is used to determine sample volume as shown in FIG. 11. An automated machine vision system is provided including a camera 322 and image processing program, which can visually determine the level of sample by intensity differences between the liquid within the sample container 324 and the headspace gas, when the vial or sample container 324 is placed in a register with a datum point and then imaged.

In still another embodiment of the invention, an initial liquid level indicator is used to determine sample volume. Specifically, a visual, magnetic, or other type of mark is stamped onto the side of the sample container at the liquid to air interface point during manufacturing. The difference between the position of the "factory" mark and the current liquid level is then determined as the amount of sample added. An advantage of this embodiment is that the accuracy can be improved by precisely measuring the original level for each and every sample container during their journey from filling to labeling and then to packaging.

In still another embodiment of the invention, a fluorescent volume exclusion substance is used to determine sample volume. A fluorescent, luminescent, phosphorescent or other type of dye is added at a specific concentration to the sample container's liquid contents at the time of manufacture. As sample is added during the collection process, the dye is diluted from its original concentration. The difference between the initial, nominal fluorescence, and the decreased fluorescence post-fill, is then detected and calculated to determine the volume of sample introduced into the container.

In still another embodiment of the invention, a method using the optical scattering pattern caused by the hemoglobin in red blood cells (RBC's) is used to determine sample volume. In this embodiment, a laser beam directed at a specific angle into the side of a blood culture container with added blood, forms a coma-shaped, light scattering pattern, and reflects part of the source energy. The appearance and shape of this scattered light pattern is similar to that of a car's headlight which forms a white orb as it is reflected in fog.

The intensity, breadth, length, decay and other parameters of this scattered light source, or orb can be measured optically and is directly related to the amount of blood introduced into the sample container. An advantage of this embodiment includes a desirable sensitivity to effects caused by different patient's hematocrits in the resulting measurements.

In a similar embodiment, a method using optical absorption, allows a user to select a light wavelength which can be used to penetrate the liquid media plus blood to reach the other side of the sample container. A photodetector there measures the relative intensity of the light getting through the sample container and uses the information to calculate the sample volume.

In still another embodiment of the invention, a nuclear magnetic resonance (NMR) apparatus is used to determine sample volume. An NMR apparatus can be used to detect the intensity of hydrogen atom spin down caused by magnetic impulse. The intensity of this signal is proportional to the number and concentration of hydrogen atoms present. In the case of a laboratory diagnostic as described herein, the hydrogen atoms would be part of the water molecules and other organic materials contained within the container's liquid volume. The NMR signal taken before and after sample fill can then be subtracted to calculate the sample volume. Additional information regarding an NMR detection apparatus is discussed in WO 99/67606, the entire content of which is incorporated herein by reference.

The above listing is not intended to be exhaustive, but is provided to illustrate the many techniques that can be applied to obtain the desired diagnostic information. The above techniques, apparatus and applications include a number of advantages. For example, immediate feedback is automatically obtained and provided to the laboratory personnel or instrument operator e.g., when a sample volume is or is not within specification. If not within specification, the lab can for example, request another sample right away so that the patient's test results are not delayed or worse, the patient's treatment is suboptimal resulting in increased morbidity or mortality. Additionally, the summary data of sample volume noncompliance, which can be automatically compiled and reported, can be used by the laboratory personnel to trace samples back to hospital services that have a high incidence so that remedial action can be used to elevate the quality of patient care.

According to an embodiment of the invention, the knowledge of sample volume can also be applied to the interpretation of other test data taken by the system 100 to, in effect, optimize the automatic detection algorithms used. For example, in the case of blood cultures, a sample volume higher than nominal contains a plethora of red blood cells which add their own metabolic activity to the metabolic activity from bacterial cells. Current blood culture instruments generally measure the production of carbon dioxide or oxygen either directly or indirectly by the cells growing in the culture media. As the patient's blood adds its own metabolic fraction, the fraction produced by any bacterial cells present can be obscured and result in a detection delay or error. Alternatively, if the blood volume added as a sample is low, the number of living bacterial cells may also be low. The culture could grow much slower than normal because of an insufficient biomass and therefore, to augment detection sensitivity, the algorithms can be tuned appropriately.

The sensing and calculation of the sample volume can also be applied to help determine the initial concentration of an adjunct biochemical, particle, cell, and the like. For example, an immunoassay or molecular probe test that is performed on the blood culture vial described above can quantify a constituent of the sample originally added (in this case the patient's blood) to predict either the likelihood of no culture growth, definitive culture growth, or a coincident medical condition such as Systemic Inflammatory Response Syndrome (SIRS).

The embodiments of the present invention described above can each be used to acquire additional information about the patient's sample automatically and apply that information to augment the utility of the diagnostic results.

Figure 12:
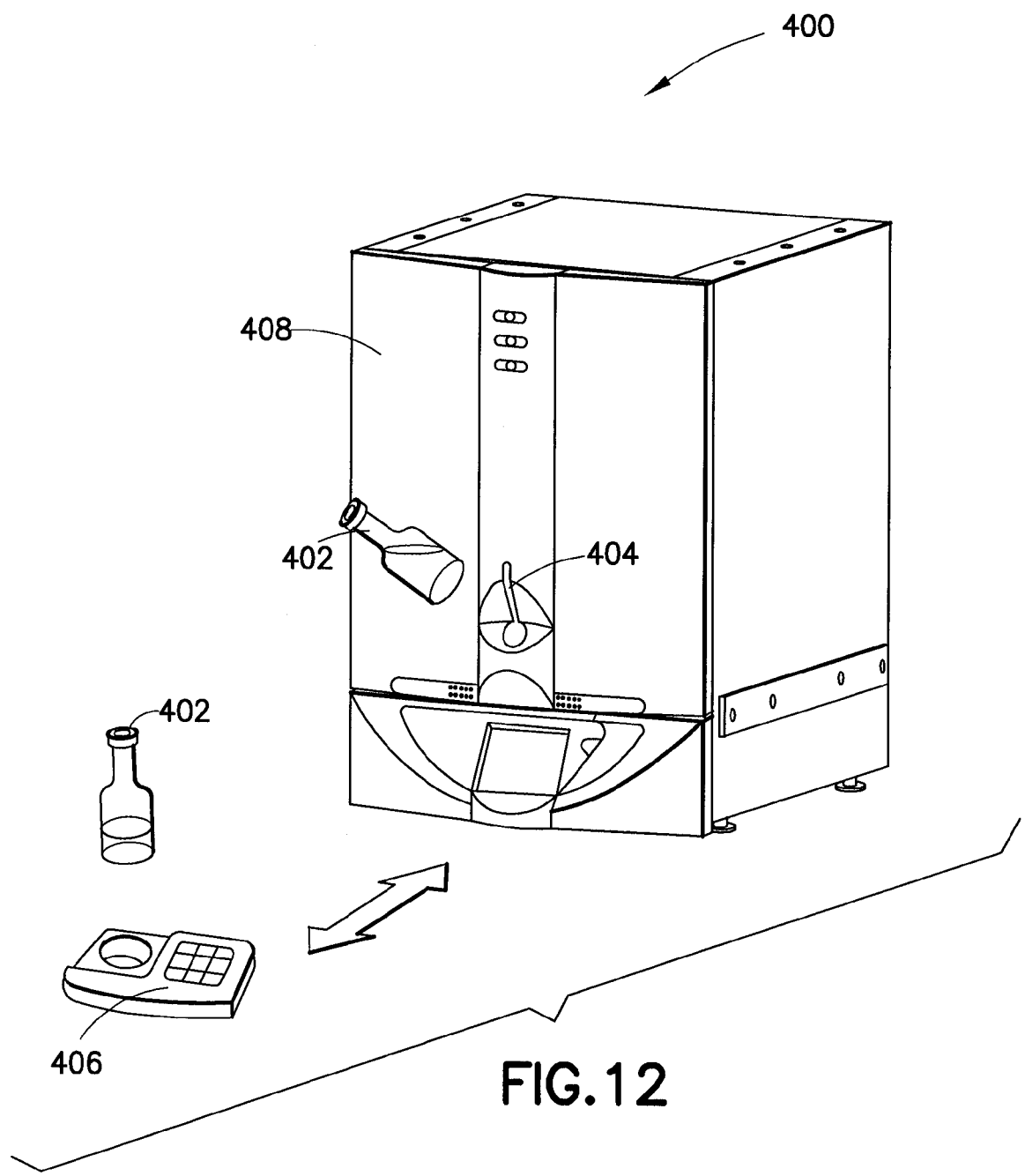
FIG. 12 is a detailed view illustrating a sample volume sensor in use with the measurement instrument shown in FIGS. 1-3.

One embodiment of the method of the invention is shown in FIG. 12. FIG. 12 is a detailed view illustrating a sample volume sensor in use with a measurement instrument such as that shown in FIGS. 1-3. The laboratorian can place a filled sample container 402 into either the sample volume sensor of 404 or 406. In FIG. 12, the sample volume sensor 404 is configured as an internal sensor, disposed within the device 408, and the sensor 406 is configured as an external sensor. The external sensor 406 can then communicate sample volume and/or barcode information with the device 408 via cabling, IR link, wireless communication, or the like. The sample volume of the vial 402 can then be determined and associated with the sample.

Figure 13:
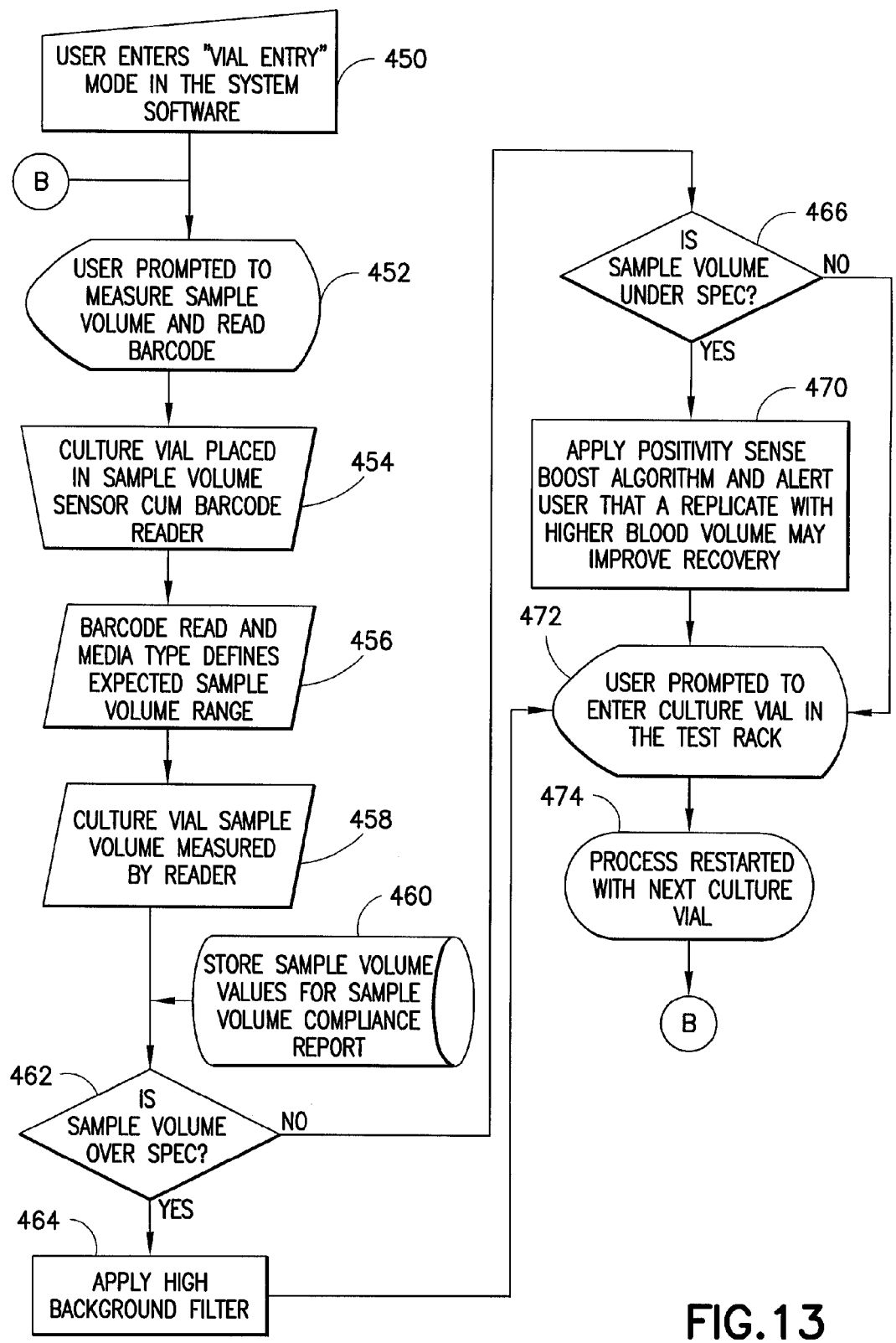
FIG. 13 is a signal processing flow diagram illustrating an exemplary method of implementing the sample volume sensor in use with the measurement instrument shown in FIGS. 1-3.

When a sample culture is to be analyzed by the incubation and measurement module, the sample culture is placed in a sample vial and the sample vial is then loaded into a respective opening in the incubation and measurement module. The incubation and measurement module can further include a keyboard, a barcode reader, or any other suitable interface that enables a technician to enter information pertaining to the sample into a database stored in a memory in the incubation and measurement module, in the central computer, or both. The information can include, for example, patient information, sample type, row and column of the opening into which the sample vial is being loaded, and the like. FIG. 13 is a signal processing flow diagram illustrating the work flow associated with this embodiment.

In a first step of FIG. 13, a technician enters "Vial Entry" mode in the system software. The technician is then prompted to measure the sample volume or "fill level" of the vial and read the associated barcode at step 452. The technician then places the culture vial in a sample volume sensor and barcode reader at step 454. The system then reads the data of the barcode and determines a container media type which is used to define an expected sample volume range at step 456. The culture vial sample volume is then measured by the reader at step 458. The sample volume value can then be stored to provide data for compliance reports at step 460.

The sample volume is then checked in steps 462 and 466. If the sample volume is over specification value at step 462, an alternate background filter is applied at step 464. An alternate background filter would delay the signal processing algorithms from detecting evidence of microbial growth. This is done so that the excessive blood fill and its effects on the chemical environment within the culture vial would have an opportunity to stabilize and have less chance to be considered a positive culture (false positive) in the absence of true microbial growth. If the sample volume is not over specification value at step 462, the sample volume is checked to determine if the sample volume is below specification value at step 466.

If the sample volume is below specification value at step 466, the system alerts the user that a replicate sample with higher blood volume may improve recovery (i.e. the probability of detecting microbes) and asks the user to keep or reject the current sample at step 470. The system then applies a positivity sense boost algorithm if the current sample is used for the test. A positivity sense boost algorithm would increase the sensitivity of the signal processing algorithms that detect evidence of microbial growth. This is done so that the lower than optimal blood fill and proportionally lower initial concentration of microbes may be detected from more subtle signal changes.

If the sample volume is not below specification value at step 466, the user is prompted to enter the culture vial into the test rack of the incubation and measurement module at step 472. The process is then restarted with the next culture vial at step 474, and returns to step 452.

By evaluating the sample volume before the introduction of the sample into the testing queue of the laboratory several advantages are met. First, the laboratory is quickly made aware if the sample that was forwarded is compliant with the culture vial manufacturer's package insert. Secondly, the sample compliance can be tracked to a particular hospital service or care-giver so that remedial training can be initiated. Thirdly, the method of culture analysis and the algorithms that are used to determine the test result can be modified and enhanced to provide better performance, efficiency, and recovery. Fourthly, by sensing and quantifying a coexistent property of the patient sample by knowing the volume added, and the concentration of analyte tested, can lead to more definitive test results and in some cases, even further or more specific diagnosis.

Additionally, the invention, though directly useful for blood culture sample handling, can be modified and applied to the collection of any sample into any sample container. In some cases, factors such as attenuation experienced in different media types may require foreknowledge of the media type to apply the correct interpretive algorithm.

In each technique described above, the results are generally superior to those achieved by checking the sample volume by eye. For example, implementation of the ultrasonic impulse sonar measurement apparatus accurately measures volumes to within 1.0 ml, and can compensate for different sample container shapes, materials, original sample volumes, sample types, medium constituents, and so forth. This technique also measures the liquid height and calculates the sample volume in a matter of seconds with a high degree of accuracy. This technique further exceeds the performance of some automated methods, such as weighing, since it avoids a possible variability in the mass of the container itself as long as internal dimensions are held within nominal limits. It is also noted that the container bottom does not need to be perfectly flat or indented as shown in the attached figure. Nevertheless, in some applications, volume measurement accuracy can be adversely affected proportionally to extreme inconsistencies in the container uniformity. As can be appreciated from the above, the embodiments of the present invention solve the problems associated with varying media fill density, varying vial geometry, container material transparency, mixture of solid, liquid, and semisolid components in the container contents, and differences in the container material, whether plastic or glass.

As noted above, various techniques can be used in the embodiment of the present invention to determine the sample volume in a container with different degrees of accuracy and repeatability, including evaluation by eye, by weight, by angle of light reflection, by optical absorption, by sonic ranging, by scattered photon migration, by chemical response, and so forth. These different methods can be provided individually or in any number of combinations to achieve the advantages as described above.

Figure 3:
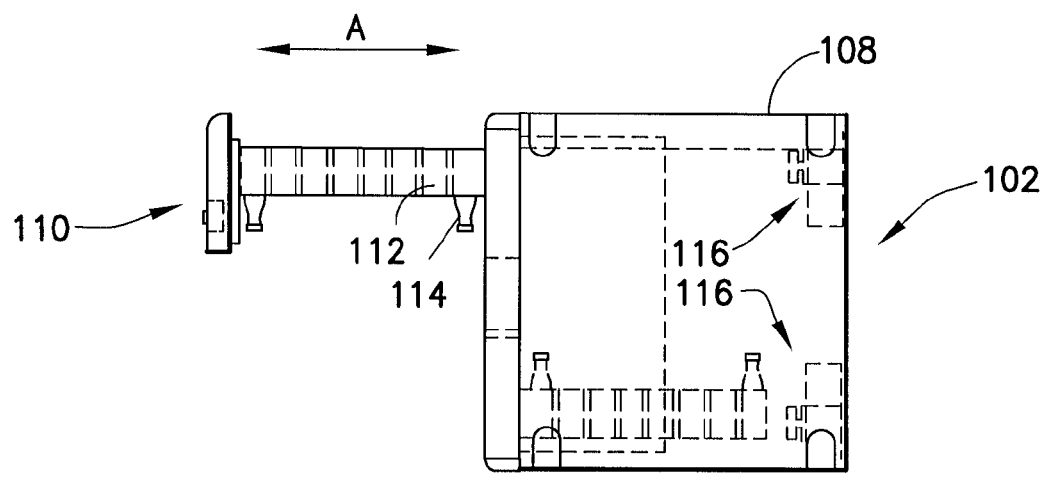
FIG. 3 is a top view of the measurement instrument shown in FIG. 2.
Figure 14:
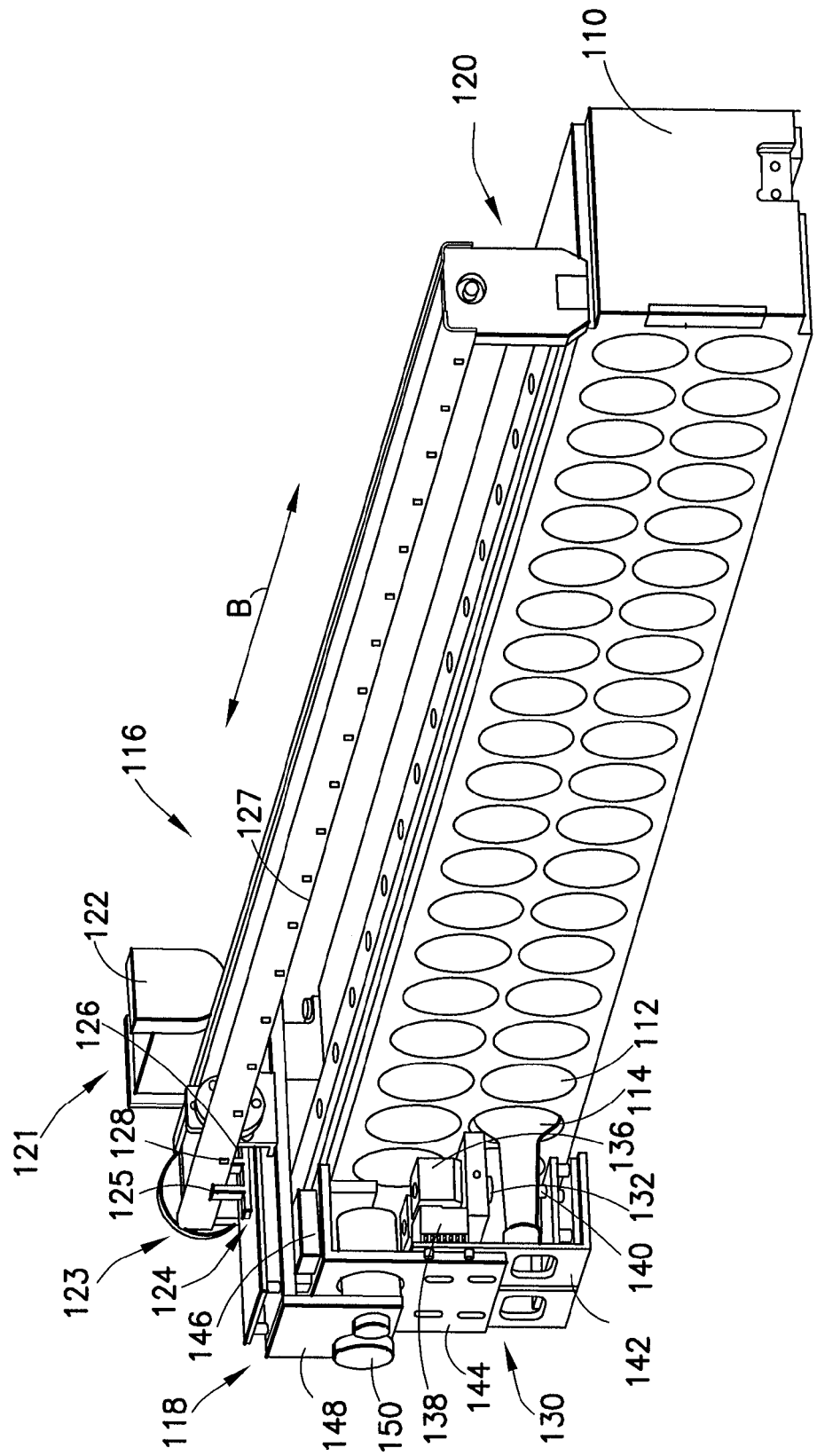
FIG. 14 is a detailed view of an example of a detector assembly employed in the measurement instrument shown in FIGS. 1-3 which uses infrared laser spectrography and/or dual wavelength modulation techniques according to an embodiment of the present invention.
Figure 15:
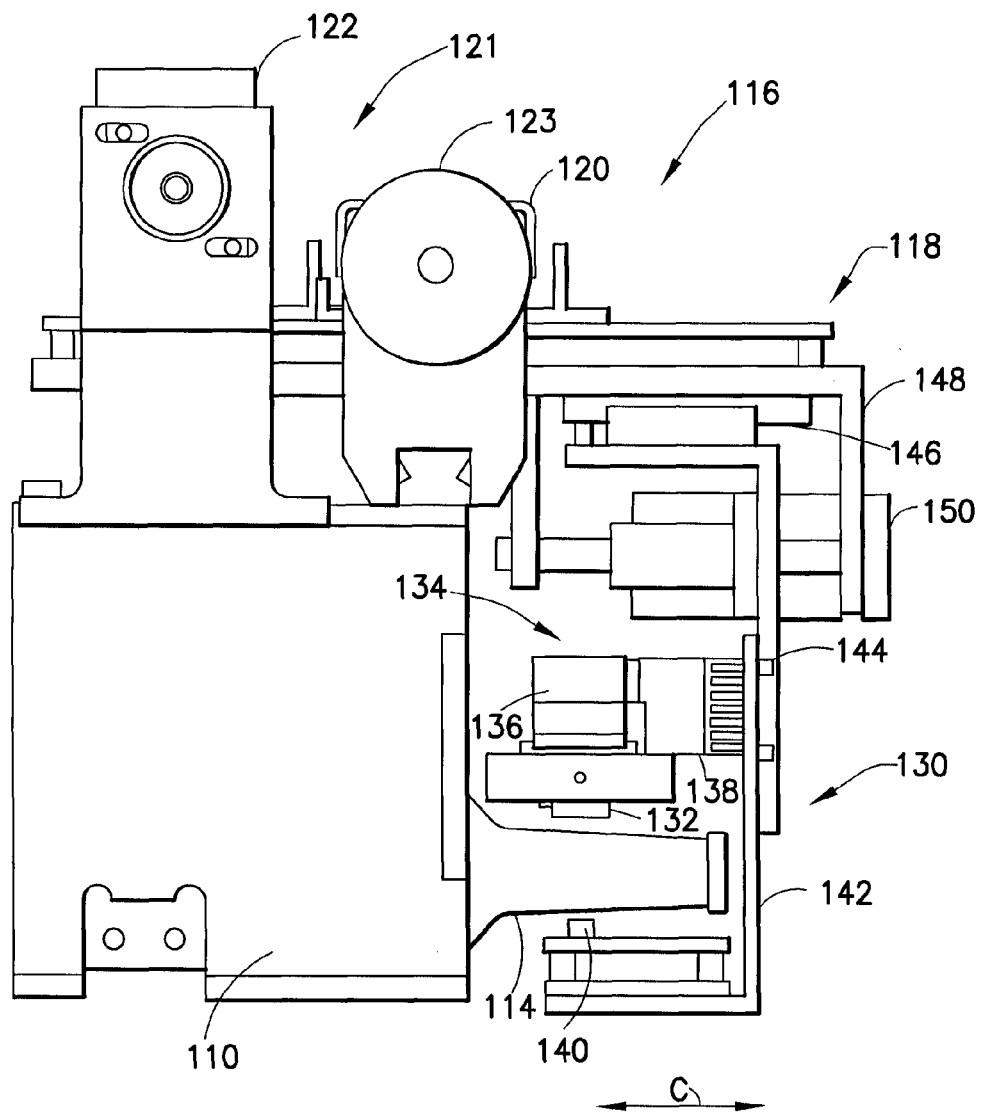
FIG. 15 is a side view of the monitoring assembly in FIG. 14.
Figure 16:
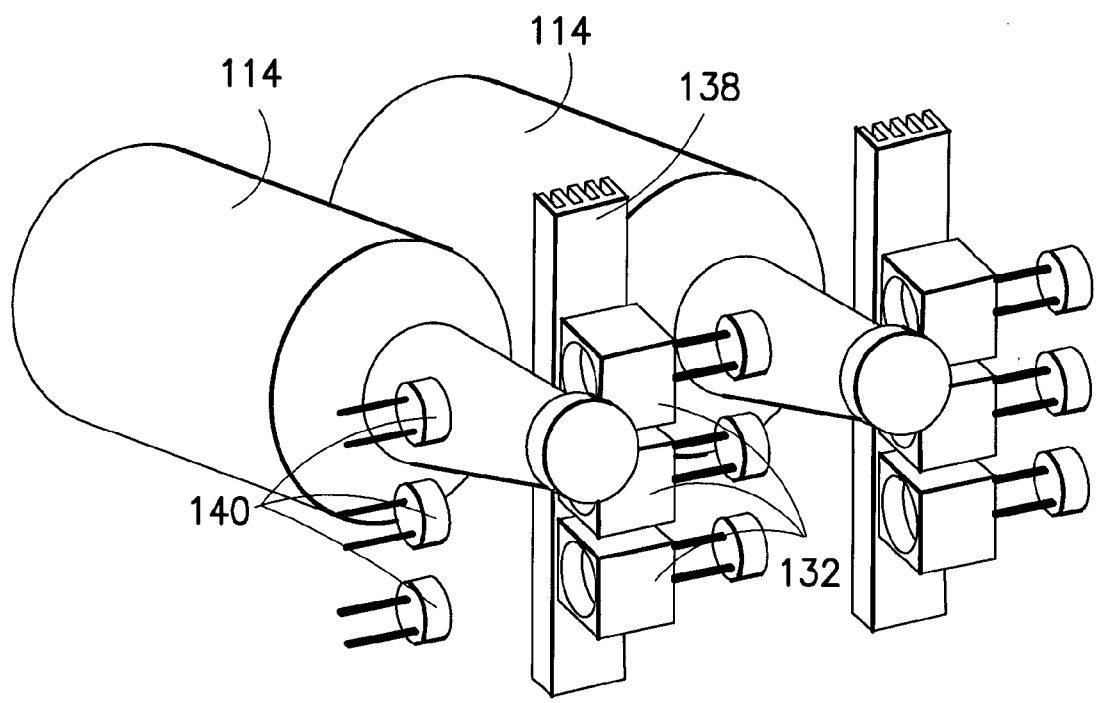
FIG. 16 is a conceptual view of a multiple laser and multiple detector arrangement employed in the monitoring assembly shown in FIGS. 14 and 15 according to an embodiment of the present invention.

The embodiment of an incubation and measurement module shown in FIG. 3, is shown in more detail in FIGS. 14-16. The incubation and measurement module 102 includes a plurality of monitoring assemblies 116, which are positioned in the incubation and measurement modules 102 to obtain readings from the sample vials 114. In the embodiment shown in FIGS. 14 and 15, each monitoring assembly 116 is configured to obtain measurements from the sample vials 114 inserted in two rows of openings 112. However, the monitoring assembly 116 can be configured to obtain readings from sample vials in any number of rows of openings as desired.

The monitoring assembly 116 includes a movable assembly 118 which, in this example, is slidably coupled to a rail assembly 120 which is fixedly coupled to the top portion of shelf 110. A motor and pulley assembly 121 comprising a motor 122, such as a DC servo motor, and a pulley arrangement 123 that is driven by the motor 122, is coupled to the rail assembly 120 and movable assembly 118. The motor 122 is controlled by, for example, the central computer 104 or a computer (not shown) in the incubation and measurement module 102 to drive the pulley arrangement 123 which, in response, slidably drives the movable assembly 118 along the rail assembly 120 in a sample vial reading direction indicated by arrow B in FIG. 14.

The moveable assembly 118 in this example further includes a sensor 124 that can comprise, for example, a light emitting device 125 and a light sensing device 126 positioned on opposite sides of a rail 127 of the rail assembly 120. As the motor and the pulley assembly 121 drives the moveable assembly 118 along rail assembly 120, the sensor 124 detects the openings 128 in the rail 126, and provides a signal indicative of this detection to the central computer 104 or a computer in the incubation and measurement module 102. The central computer 104 or a computer in the incubation and measurement module 102 uses this detection signal to monitor the position of the moveable assembly 118 along the rail assembly 120. Also, because each opening 128 corresponds to a respective column of openings 112 in the shelf 110, the computer can determine which sample vials 114 are being read by the detectors in the moveable assembly 118 of monitoring assembly 116 as described in greater detail below.

The moveable assembly 118 can include a plurality of detector units 130, the number of which corresponds to the number of rows of sample vials 114 that the monitoring assembly 116 is configured to read. That is, if the monitoring assembly 116 is configured to read two rows of sample vials 114, the movable assembly 118 will include two detector units 130. For illustration purposes, FIGS. 14 and 15 show only one detector unit 130.

In an alternate arrangement, the movable assembly 118 can be configured to scan in an x-y direction to take readings from the sample vials 114. That is, the movable assembly 118 can be configured to scan back and forth along the rows of sample vials 114 to therefore take readings from the entire array of sample vials 114.

As shown in FIGS. 14 and 15, each detector unit 130 includes at least one laser 132 which, in this example, is an infrared diode laser, to monitor the concentration of a gas or the pressure in the sample vials. The laser 132 is coupled to a laser assembly 134, which includes a cooling and heating device 136 that can cool or heat the laser 132 to tune the frequency of the light being emitted by the laser 132. As the laser 132 emits light having a single frequency, a controller (e.g., controller 154 shown in FIG. 7 and described in greater detail below) can control the cooling and heating device 136 to change this frequency, thus enabling the laser 132 to scan using a range of frequencies. The laser assembly 134 further includes a heat sink 138 that can dissipate heat from the cooling and heating device 136, and thus, aid in controlling the temperature of the laser 132.

As further illustrated in FIG. 15, each detector unit 130 also includes a detector 140 that is mounted to receive the light being emitted by the laser 132. In this example, the detector 140 is an infrared light detector capable of detecting infrared light having the wavelength(s) of the light emitted by the laser 132.

The laser 132, laser assembly 134, and detector 140, are coupled to a laser and detector mounting bracket 142, which is further coupled to a movable mounting bracket 144. The movable mounting bracket 144 is coupled via slide rails 146 to a fixed mounting bracket 148. The fixed mounting bracket 148 is coupled with rail assembly 120 for movement along the rail assembly 120 by the motor and pulley assembly 121.

A motor 150 is coupled to the movable mounting bracket 144 and is controlled by the central computer 104 or a computer in the incubation and measurement module 102, to move the movable mounting bracket 144 in a direction along arrow C as shown in FIG. 15. The motor 150 can thus position the laser 132 and detector 140 at the appropriate location along the neck of sample vial 114 to obtain the most accurate readings as discussed in greater detail below. Also, as can be appreciated from the above description, by moving the fixed mounting bracket 148 along the rail assembly 120, the motor and pulley assembly 121 translates the entire movable assembly 118, including the laser 132 and detector 140, in a direction along arrow B as shown in FIG. 14. This movement positions the laser 132 and detector 140 at the necks of the sample vials 114 in the rows of sample vials 114.

In addition, for illustration purposes, FIGS. 14 and 15 each show only a single laser 132 and a single detector 140. However, as shown conceptually in FIG. 6, the laser and detector mounting bracket 142 can have a plurality of lasers 132 and a plurality of detectors 140 mounted thereto. In FIG. 16, three lasers 132 and three corresponding detectors 140 are shown. As described in greater detail below, each laser 132 can emit infrared light having a particular wavelength based on the type of gas that is to be detected in the sample vials 114. For example, one laser 132 can emit infrared laser light having a wavelength appropriate for detecting carbon dioxide, another laser 132 can emit infrared laser light having a wavelength appropriate for detecting oxygen, and the third laser 132 can emit infrared laser light having a wavelength appropriate for detecting another type of gas. Also, each detector 140 is disposed at an opposing position to detect light from a respective laser 132 as shown.

Figure 17:
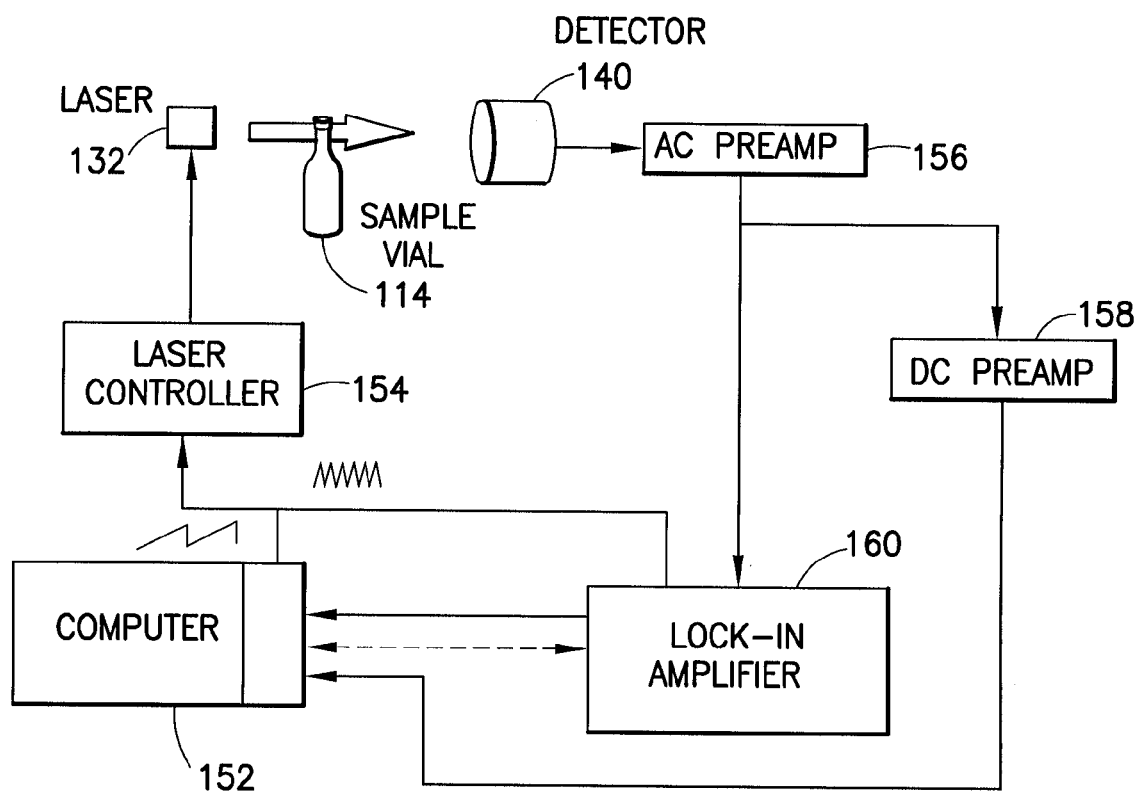
FIG. 17 is a block diagram of an example of the electronic components used by the monitoring assembly to monitor the concentration of one or more gasses or pressure in the sample vials according to an embodiment of the present invention.

FIG. 17 is an exemplary schematic illustrating the components provided for reading a sample vial 114 in accordance with an embodiment of the present invention. As shown in FIG. 17, once a laser 132 and corresponding detector 140 have been positioned with respect to a sample vial 114 to be read, a computer 152, which can be included in the central computer 104 or in incubation and measurement module 102, controls a laser controller 154 to control the laser 132 to emit an infrared laser light toward the neck of the sample vial 114. The laser light that passes through sample vial 114 is detected by detector 140, which converts the detected laser light into an electrical signal and provides the electrical signal to an AC preamplifier 156. As can be appreciated by one skilled in the art, the AC preamplifier 156 performs an AC amplification on the electrical signal and provides the amplified signal to a DC preamplifier 158 and a lock-in amplifier 160. The DC preamplifier 158 and the lock-in amplifier 160 further amplify the electrical signal and provide the further amplified electrical signal to the computer 152.

The computer 152 receives and interprets the amplified signal to determine whether any of the infrared laser light emitted by laser 132 has not been detected by detector 140, thus indicating that some of the laser light has been absorbed by a gas within the sample vial 114. The computer 152 can thereafter, determine the type and concentration of the gas and, if desired, the pressure inside the sample vial 114 based on the amplified electrical signal using suitable algorithms as described in detail in the U.S. Pat. No. 6,709,857 referenced above.

While various embodiments have been chosen to demonstrate the invention, it will be understood by those skilled in the art that various modifications and additions can be made without departing from the scope of the invention.

What is claimed is:

1. A method for the detection of a pathogen in a biological fluid sample comprising the steps of:
   determining the volume of a biological fluid sample in a plurality of sample containers comprising said biological fluid sample, a growth medium, and an environment using a sample volume sensor device and, based on a volume measurement determined from the volume sensor device, automatically determining that the biological fluid sample volume is either within specification or not;

prompting a user either to elect to further process sample containers that contain the volume of biological fluid sample determined to be outside volume specifications based on a signal from the sample volume sensor device or to reject biological fluid samples that are outside volume specification;

incubating the elected sample containers having biological fluid sample outside the volume specification;

measuring one or more parameters within the environment of the elected sample containers;

providing a detection signal indicative of the one or more measured parameters within the environment; and processing the detection signal via a signal processing algorithm for determining evidence of pathogenic growth within the elected sample containers, and if the volume of biological fluid sample in the elected sample containers was determined to be over volume specification, automatically applying an alternate background filter that delays the processing step for a period of time based on the volume measurement determined from the volume sensor device, or if the volume of biological fluid sample was determined to be below volume specification, automatically applying a positivity sense boost algorithm that increases the sensitivity of the signal processing algorithm to changes in the detection signal that are indicative of changes in the one or more parameters.

2. The method of claim 1 wherein the incubating step comprises:
placing said container in an incubation and measurement module.

3. The method of claim 2 wherein the step of determining the volume of said sample comprises:
placing said container in a sample volume sensor separate from the incubation and measurement module.

4. The method of claim 2 wherein the step of determining the volume of said sample comprises:
placing the container in a sample volume sensor disposed on or within the incubation and measurement module.

5. The method of claim 1 wherein the step of determining the volume of said sample comprises:
measuring the height of the sample in the container, and calculating the sample volume from the sample height measurement.

6. The method of claim 5 wherein said sample height is measured by ultrasonic reflectometry.

7. The method of claim 5 wherein said sample height is measured by a laser displacement sensor.

8. The method of claim 5 wherein the sample height is measured by a through beam optical sensor.

9. The method of claim 5 wherein said sample height is measured by a laser scanning photodiode array.

10. The method of claim 5 wherein said sample height is measured by a refractive index, internal reflection apparatus.

11. The method of claim 5 wherein said sample height is measured by a retro-reflective optical detection apparatus.

12. The method of claim 5 wherein said sample height is measured by a machine vision apparatus.

13. The method of claim 1 wherein the sample volume is determined by a capacitive proximity detection apparatus.

14. The method of claim 1 wherein said sample volume is determined by measurement of sample weight.

15. The method of claim 1 wherein the step of determining the volume of said sample comprises;
providing a fluorescent, luminescent or phosphorescent dye at a specific concentration in the sample container prior to introducing the biological fluid sample,
measuring the fluorescence, luminescence or phosphorescence, of said dye and sample, and
calculating said sample volume from the difference in initial and subsequent fluorescence, luminescence or phosphorescence measurements.

16. The method of claim 1 wherein said sample volume is determined by optical scattering.

17. The method of claim 1 wherein said sample volume is determined by nuclear magnetic resonance.

18. A method for the detection of a pathogen in a biological fluid sample comprising the steps of:
determining the volume of a biological fluid sample in a plurality of sample containers comprising the biological fluid sample and a growth medium using a sample volume sensor device;
communicating the sample volume to one or more user interfaces;
comparing the sample volume determined by the sample volume sensor to that of a sample volume specification;
if the sample volume is outside of the sample volume specification, providing a corresponding message to the one or more user interfaces;
responding to a user input regarding said message;
selecting samples outside of the sample volume specification for incubation based upon the user input;
incubating the selected samples;
monitoring one or more parameters in the incubated samples indicative of growth of the pathogen;
providing a detection signal indicative of the one or more parameters to a computer; and
applying a signal processing algorithm to the detection signal to detect evidence of pathogenic growth, wherein:
where the sample volume is determined to be above specification, the application of the signal processing algorithm to the detection signal is automatically delayed until the one or more parameters stabilize,
where the sample volume is determined to be below specification, the sensitivity of the signal processing algorithm to changes in the detection signal is automatically increased.

19. The method of claim 18 further comprising the step of:
prompting the user to place the sample container into a test rack of an incubation and measurement module if the sample volume value is within the sample volume specification.

20. The method of claim 18 further comprising the step of:
storing the determined sample volume for sample volume specification compliance reports.

21. The method of claim 18 further comprising the step of:
calculating the initial concentration of the pathogen in the sample using the determined sample volume.

* * * * *